US006357673B1

(12) United States Patent
Condon

(10) Patent No.: US 6,357,673 B1
(45) Date of Patent: Mar. 19, 2002

(54) TWO PRONG PROFESSIONAL SPRAYER ASSEMBLY WITH AGITATOR AND FILTER

(75) Inventor: Gregory C. Condon, Batavia, NY (US)

(73) Assignee: Chapin Manufacturing, Inc., Batavia, NY (US)

( * ) Notice: Subject to any disclaimer, the term of this patent is extended or adjusted under 35 U.S.C. 154(b) by 0 days.

(21) Appl. No.: 09/448,790

(22) Filed: Nov. 24, 1999

Related U.S. Application Data

(60) Provisional application No. 60/110,186, filed on Nov. 30, 1998.

(51) Int. Cl.[7] .......................... A61M 11/02; B05B 9/04; A01G 25/14

(52) U.S. Cl. ........................ 239/373; 239/375; 239/378

(58) Field of Search .............................. 222/226, 189.1, 222/372, 382, 383.1, 385, 464.1; 239/1, 142–144, 152–154, 373, 375, 378, 553, 320–323

(56) References Cited

U.S. PATENT DOCUMENTS

| | | | | | |
|---|---|---|---|---|---|
| 851,758 | A | * | 4/1907 | Kauffman | 239/373 |
| 921,594 | A | * | 5/1909 | Crane | 239/373 |
| 1,134,354 | A | | 4/1915 | Seifke | |
| 2,580,132 | A | | 12/1951 | Seymour | |
| 2,816,692 | A | * | 12/1957 | Schade | 239/373 |
| 3,099,394 | A | * | 7/1963 | Lynn | 239/373 |
| 3,412,937 | A | | 11/1968 | Chamberlain | |
| 3,570,819 | A | * | 3/1971 | Rosinger | 239/108 |
| 3,831,850 | A | | 8/1974 | Hunter | |
| 4,253,772 | A | | 3/1981 | Burton-Smith | |
| 4,362,256 | A | * | 12/1982 | Polasek | 222/383 |
| 4,377,130 | A | * | 3/1983 | Schwieger | 119/51.5 |
| 4,875,781 | A | | 10/1989 | Raska | |
| 4,880,312 | A | | 11/1989 | Carlson | |
| 4,950,082 | A | | 8/1990 | Carlson | |
| 5,320,248 | A | | 6/1994 | Jamieson, III | |

FOREIGN PATENT DOCUMENTS

| | | | | |
|---|---|---|---|---|
| FR | 762607 | * | 10/1933 | 239/373 |

* cited by examiner

*Primary Examiner*—David A. Scherbel
*Assistant Examiner*—Davis Hwu
(74) *Attorney, Agent, or Firm*—Jaeckle Fleischmann & Mugel, LLP

(57) ABSTRACT

A sprayer assembly for dispensing a fluid having suspended therein particulate matter of a particulate size includes a reservoir. The fluid to be sprayed is contained in the interior of the reservoir. The reservoir includes a first opening for receiving the fluid and a second opening for dispensing the fluid. A pump is received in the first opening and includes a pump handle disposed exterior to the reservoir and a pump mechanism disposed in the reservoir interior. The pump is operable to increase the pressure in the reservoir interior. A discharge tube has an outlet end fluidly connected to the reservoir second opening and an intake end disposed in the reservoir interior. A filter having a plurality of filter passages is disposed within the reservoir interior and is associated with the intake end of the discharge tube. The filter prevents particles larger than the particulate size from passing into the discharge tube. An agitator is disposed in the reservoir interior and creates a fluid turbulence around the filter and thereby dislodges accumulated particles from around the filter and from the filter itself.

19 Claims, 3 Drawing Sheets

TWO PRONG PROFESSIONAL SPRAYER ASSEMBLY WITH AGITATOR AND FILTER

CROSS REFERENCE TO RELATED APPLICATIONS

This application claims the benefit of U.S. Provisional Application No. 60/110,186, filed Nov. 30, 1998.

FIELD OF THE INVENTION

The present invention relates to a pump sprayer assembly for the spraying of liquids or fluids. More particularly, the present invention relates to a pump sprayer for spraying fluids which contain a solid particulate matter or powder in solution or suspension therein.

DESCRIPTION OF THE RELATED ART

Pump sprayers are typically used for dispensing fluids such as cleaning fluids, insecticides, fertilizers and various other liquids. Conventional pump sprayers include a supply tank or reservoir dimensioned to hold a predetermined volume of liquid, a manual pump or piston, a pressure vessel or accumulator, a discharge valve, and a spray wand with a nozzle from which the fluid is discharged. In some conventional pump sprayers, the reservoir or supply tank performs its intended function and also serves the function of the accumulator or pressure vessel. In operation, the reservoir initially contains air at atmospheric pressure and the fluid to be sprayed. The operation of the pump forces air into the reservoir, thereby increasing the pressure of the air therein. The compressed air, in turn, exerts pressure on the fluid contained in the reservoir. Operation of the discharge valve allows the pressure within the accumulator to push the fluid out through the nozzle until the valve is closed or equilibrium is reached.

Conventional pump sprayers are not adapted for the spraying of fluid containing solid particulate matter suspended therein. Particulate matter which is suspended in a fluid tends after a period of time to settle out of suspension from within the fluid. Conventional sprayers generally fail to provide a means for maintaining the particulate matter in solution or suspension. Therefore, such a fluid applied from a conventional sprayer is likely to contain an amount of the particulate matter that is not optimal.

The particulate matter typically settles at or near the bottom of the reservoir of the sprayer. Conventional sprayers generally intake the fluid to be discharged from a location which is at or near the bottom of the reservoir. Thus, intake occurs at or near the area in which settled particulate has accumulated. This results in the intake by the sprayer of fluid having an increased concentration of solid particulate matter. This increased concentration of particulate may be significantly higher than the intended or recommended concentration. In use, such an increased concentration of particulate near the intake may result in over application. The potential exists for the application of excessive, perhaps even dangerous, concentrations of the active ingredient in the applied fluid, such as pesticide or fertilizer, and may result in damage or injury to property, plants, animals, or perhaps the user of the pump sprayer. After the portion of the fluid that contains a higher concentration of particulate due to settling is discharged, the situation reverses and the opposite problem occurs. The remaining fluid will have a lower than intended concentration of particulate. The concentration may be low enough to render the particular fluid ineffective for its intended use.

Furthermore, conventional sprayers tend to become clogged by the particulate matter suspended within the fluid. As referred to above, the particulate matter tends to settle out of solution with the fluid and accumulate near the bottom of the reservoir proximate the intake. The settled particulate matter results in a reduced volume of fluid in the region surrounding the intake and, therefore in a reduced volume of fluid being dispensed from the sprayer at a given pressure. Over time, this high concentration of settled particulate may clog the intake itself, the spray nozzle, or any various other points along the discharge path. Such clogging requires a user to dismantle the sprayer and remove any clogs by manually cleaning the sprayer. This process is time consuming and can be, depending on the particular sprayer, of moderate complexity. Furthermore, the process of clearing a clog may expose the user to hazardous chemicals.

Adding a filter to the intake of a conventional sprayer will not completely alleviate the problem of reduced fluid flow or of clogging. As settling of the particulate matter occurs, the particulate matter accumulates on and around a filter. Other particles and foreign substances having a particulate size larger than the filter passages also accumulate on and around the filter. The settled and foreign accumulated particulate matter displaces the fluid from the region surrounding the filter and, therefore, restricts the volume of fluid being discharged from the sprayer. A clog results when the pressure within the reservoir is insufficient to impart enough energy to enable the fluid to displace or flow through the accumulated particulate matter. Furthermore, simply increasing the pressure upon the fluid tends to exacerbate the clog. Under increased pressure, the fluid simply pushes the accumulated particles more strongly against a filter. When the concentration of accumulated particulate matter reaches a certain point, increased pressure alone will not provide the fluid with enough energy to flow through or displace the particles. Thus, a conventional sprayer having a filtered intake that is being used to dispense fluid having particulate matter suspended therein may still clog. The timely, complex, and potentially hazardous process of disassembly being required in order to remove the clog.

What is needed in the art is a sprayer assembly for the spray application of a fluid containing solid particulate matter suspended therein which will: prevent the settling of the particulate matter out of solution with the fluid; return settled particulate matter into suspension with the fluid; provide improved resistance against clogging; and provide a way to dislodge particulate matter that has accumulated on and around the sprayer intake.

SUMMARY OF THE INVENTION

The present invention provides a sprayer assembly for sprayingly dispensing a fluid having particulate matter in suspension therein.

The invention comprises, in one form thereof, a sprayer assembly including a reservoir. The fluid to be sprayed is contained in the interior of the reservoir. The reservoir includes a first opening for receiving the fluid and a second opening for dispensing the fluid. A pump is received in the first opening and includes a pump handle disposed exterior to the reservoir and a pump mechanism disposed in the reservoir interior. The pump is operable to increase the pressure in the reservoir interior. A discharge tube has an outlet end fluidly connected to the reservoir second opening and an intake end disposed in the reservoir interior. A filter having a plurality of filter passages is disposed within the reservoir interior and is associated with the intake end of the discharge tube. The filter prevents particles larger than the particulate size from passing into the discharge tube. An agitator is disposed in the reservoir interior and creates a fluid turbulence around the filter and thereby dislodges accumulated particles from around the filter and from the filter itself.

An advantage of the present invention is that the filter allows fluid to enter from all sides and therefore provides improved resistance against particulate matter clogging the filter.

Another advantage of the present invention is that the agitator creates a turbulence in the liquid contained in the reservoir of the sprayer thereby maintaining particulate matter in suspension with the liquid. Thus, proper concentration of particulate matter in the fluid being discharged from the sprayer is maintained.

Yet another advantage of the present invention is that the turbulence in the liquid occurs in a region surrounding the filter. The turbulence dislodges settled particulate matter from that region and from the filter itself. Thus, it is ensured that a full volume of fluid is dispensed at a given pressure and clogs are prevented.

BRIEF DESCRIPTION OF THE DRAWINGS

The above-mentioned and other features and advantages of this invention, and the manner of attaining them, will become apparent and be better understood by reference to the following description of one embodiment of the invention in conjunction with the accompanying drawings, wherein.

Figure 1:
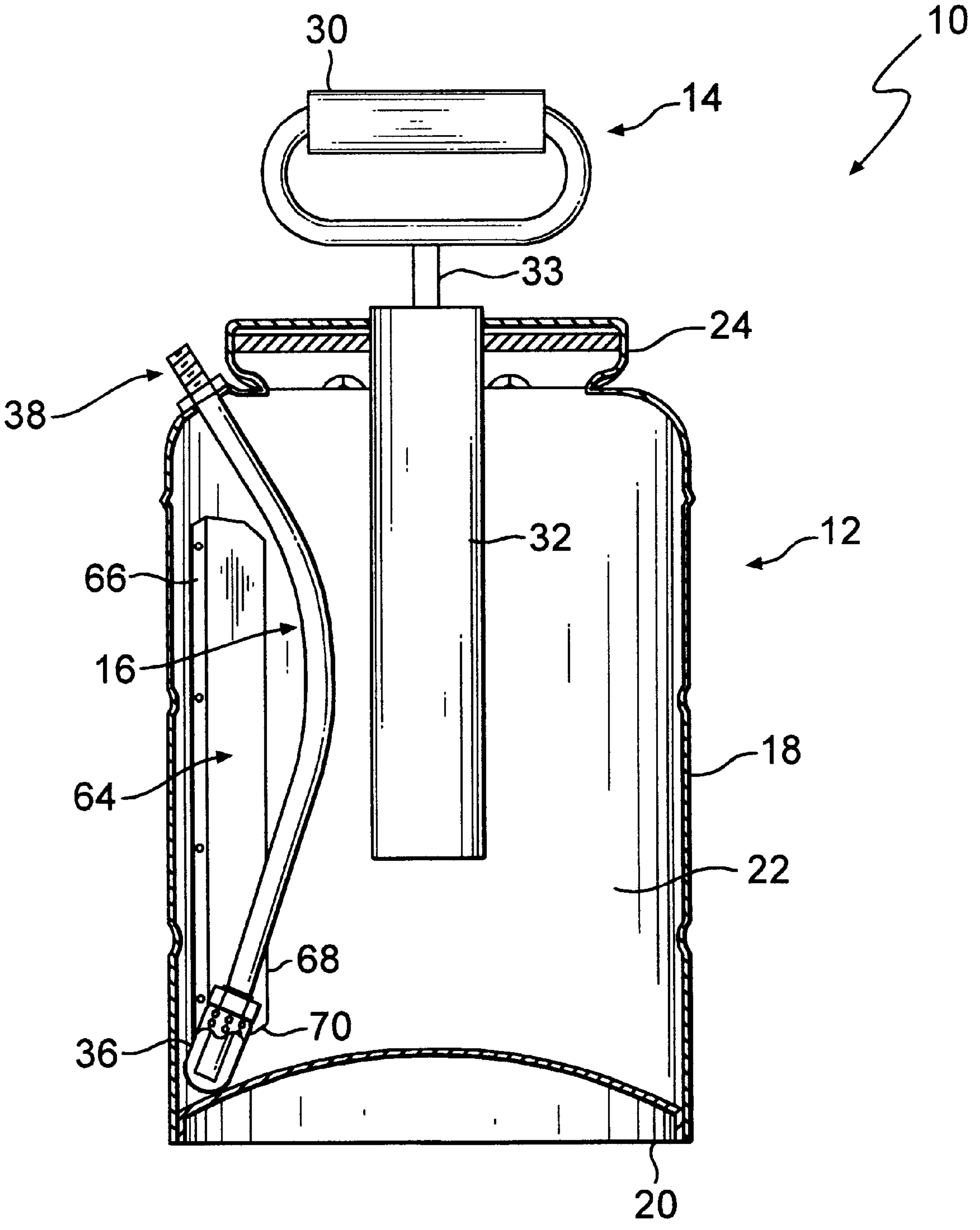
FIG. 1 is a perspective, partially sectioned view of one embodiment of a sprayer assembly of the present invention.
Figure 2:
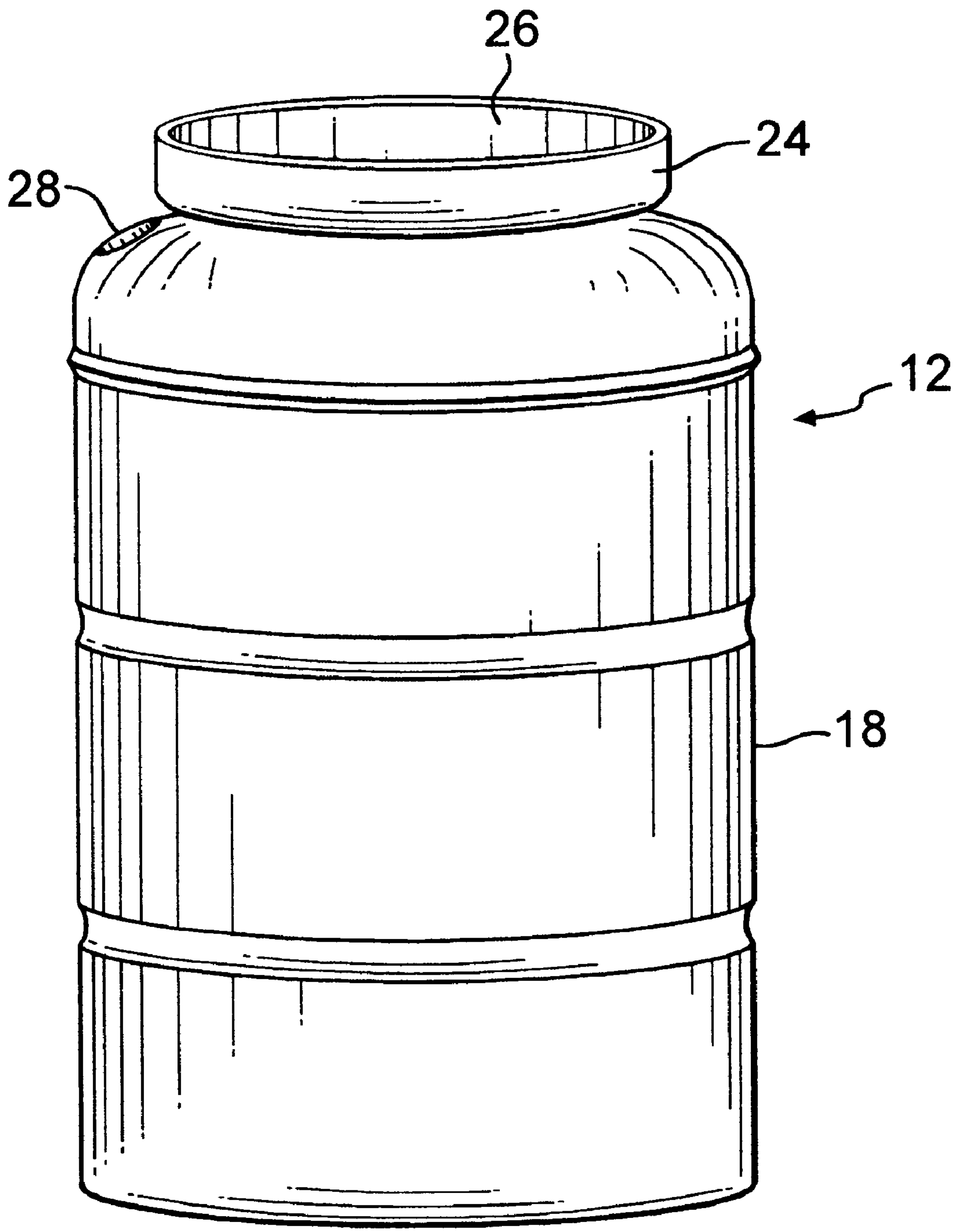
FIG. 2 is a perspective view of the reservoir of the sprayer assembly of FIG. 1.
Figure 3:
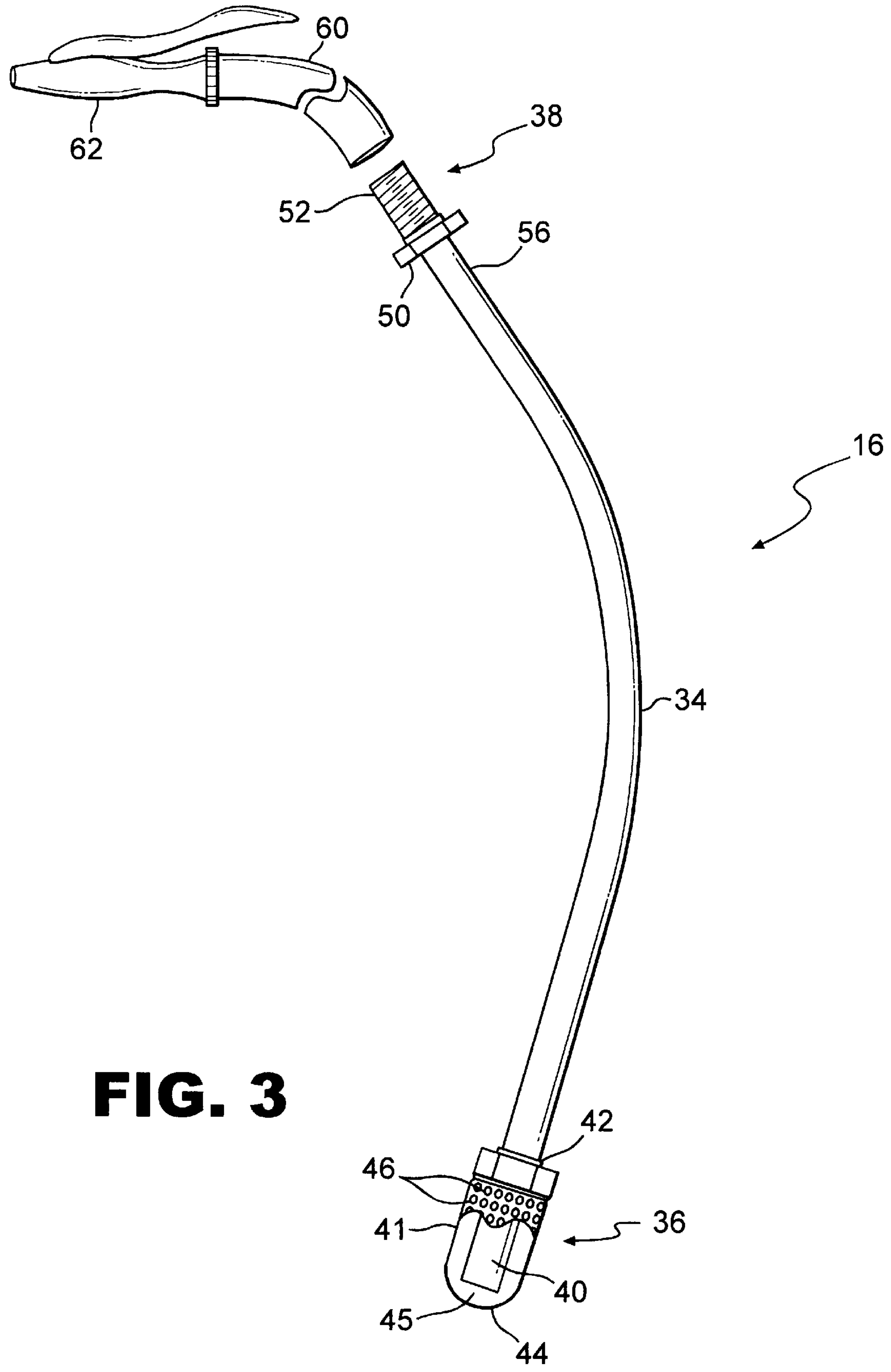
FIG. 3 is a perspective view of the outlet assembly of FIG. 1.

The exemplification set out herein illustrates one preferred embodiment of the invention, in one form, and such exemplification is not to be construed as limiting the scope of the invention in any manner.

DETAILED DESCRIPTION OF THE INVENTION

Referring now to the Figures, there is shown a sprayer assembly 10 including a reservoir 12, a pump assembly 14, and outlet assembly 16.

Reservoir 12 is substantially cylindrical in shape, having a reservoir wall 18 and a bottom side 20. Reservoir wall 18 and bottom side 20 conjunctively define interior 22 of reservoir 12. Neck 24 is formed by reservoir wall 18 and defines a fill opening 26. Fill opening 26 is made sufficiently large, such as, for example, at least four inches in diameter, to facilitate cleaning and ease of filling of reservoir 12. Outlet assembly 16 is connected to discharge opening 28 through which fluid held within interior 22 of reservoir 12 is dispensed. Reservoir 12 is dimensioned to hold a predetermined volume of fluid, and is formed of a material, such as, for example, aluminum, stainless steel, or fiberglass, having sufficient strength and physical characteristics to contain the fluid to be sprayed. Sprayer assembly 10 will typically be used to apply chemical compositions comprising a fluid having a particulate matter suspended therein, such as insecticide or cleaning fluids. Therefore, reservoir 12 must be formed from materials that are inert to such chemicals. Further, the material from which reservoir 12 is formed must be capable of withstanding pressure created therein by the operation of pump assembly 14.

Pump assembly 14 includes handle 30 interconnected to pump mechanism 32 by shaft 33. The pump assembly 14 is received within fill opening 26. Pump assembly 14 and fill opening 26, when assembled, form a tight seal which prevents the ingress or egress of air or fluid from interior 22 of reservoir 12. The seal (not shown) may be formed by, for example, a compressible rubber or fiber gasket secured to the periphery of fill opening 26 and a clamping device (not shown) to clamp a surface (not shown) of pump assembly 14 against the gasket, thereby sealing interior 22.

Outlet assembly 16 includes discharge tube 34, filter 36, and fitting 38. Filter end 40 of discharge tube 34 extends into and is surrounded by filter 36. The material from which discharge tube 34 is constructed must be inert to the chemical compositions referred to above which sprayer 10 is likely to be used to apply. Discharge tube 34 is formed of a semi-rigid material, such as, for example, a metal reinforced rubber or plastic tube. For reasons discussed hereinafter, discharge tube 34 must be sufficiently rigid to ensure filter 36 remains disposed proximate bottom 20 of reservoir 12 when reservoir 12 is filled with fluid.

Filter 36 includes a substantially cylindrical body portion 41, which defines opening 42 at one end thereof, and a semispherical portion 44. Filter 36 is disposed proximate to bottom 20 of reservoir 12. A plurality of filter passages 46 of a predetermined size are formed on substantially the entirety of body portion 41 and semispherical portion 44. Discharge tube 34 is received through opening 42 into body 41 of filter 36. Discharge tube 34 is disposed within body 41 of filter 36 such that filter end 40 of discharge tube 34 is disposed proximate semispherical portion 44. Thus, a portion of discharge tube 34 extends into and is surrounded by filter 36. A gap 45 of, for example, approximately one-quarter inch is purposefully provided between semispherical portion 44 and filter end 40 of discharge tube 34 for reasons discussed hereinafter. Filter 36 is attached to discharge tube 34 by use of, for example, an inert fluid-resistant, sealing adhesive. Filter 36 is constructed of, for example, a fine metal mesh or screen.

The shape of filter 36 acts to prevent plugging of the filter by allowing fluid which is carrying particulate matter in suspension therewith to enter filter 36 from all directions. The gap 45 between semispherical portion 44 and filter end 40 of discharge tube 34 also acts to prevent immediate plugging of the filter. Filter 36 is disposed proximate to bottom 20 of reservoir 12 in order to maximize the amount of fluid which can be discharged from reservoir 12 before refilling thereof is required. As particulate matter settles out of suspension with the fluid, the particulate matter will tend to accumulate at or near the bottom 20 of reservoir 12. Thus, semispherical portion 44 of filter 36 is disposed in an area where settled particulate matter may accumulate, thereby constricting or blocking certain of the plurality of filter passages 46 positioned at or near semispherical portion 44. The gap 45 between semispherical portion 44 of filter 36 and filter end 40 of discharge tube 34 permits fluid and particulate matter in suspension therewith that has entered filter 36 from an area that is not constricted by settled particulate matter to enter discharge tube 34.

Filter passages 46 are of a predetermined size. Passages 46 permit particles of a certain size to pass through the filter 36 and enter discharge tube 34 and prevent particles that exceed the predetermined size from passing. The size of filter passages 46 is selected to closely match the size of particulate matter typically found in suspension with a selected category or classification of fluid, such as, for example, insecticides. Thus, the intended particulate matter will pass freely through filter 36 while particulate matter that has coagulated, fallen out of suspension, or is of a larger size will be blocked from passing through filter 36 and into discharge tube 34.

Fitting 38 includes an inlet side 50 and an outlet side 52. Fitting end 56 of discharge tube 34 is attached to fitting 38 by use of, for example, an inert fluid-resistant, sealing adhesive. Fitting 38 is received within discharge opening 28 and sealingly attached to reservoir 12. The attachment of fitting 38 to reservoir 12 is by use of, for example, an inert fluid-resistant, sealing adhesive or by welding. The outlet side 52 of fitting 38 is threaded to receive spray tube 60, which is terminated by a pressure control valve 62 operable to discharge fluid from reservoir 12.

Agitator 64 is an elongate planar member having a first elongate edge 66, a second elongate edge 68 and an agitator end 70. Agitator 64 is attached at first elongate edge 66 to the interior of reservoir wall 18 by, for example, spot welding or adhesive. Agitator 64 projects away from reservoir wall 18 a predetermined distance into interior 22 of reservoir 12 such that second elongate edge 68 is disposed substantially within the interior 22 of reservoir 12 As noted above, filter 36 is disposed proximate to bottom 20 of reservoir 12. Agitator end 70 is disposed a predetermined distance from bottom 20 of reservoir 12 such that at least a portion of filter 36 is disposed more proximate to the bottom 20 than is agitator end 70. In other words, filter 36 overlaps agitator end 70 relative to bottom 20 of reservoir 12.

In use, pump assembly 14 is removed from fill opening 26, thereby exposing the fill opening and rendering interior 22 of reservoir 12 accessible for being filled with fluid. Reservoir 12 is then filled with a fluid, such as, for example, a pesticide, having particulate matter suspended therein. Pump assembly 14 is thereafter replaced and sealed to reservoir 12. Air within reservoir 12 is, initially, at atmospheric pressure. Pump assembly 14 is operated to increase the pressure of the air trapped within interior 22 of reservoir 12. When pressure valve 62 is actuated, opening the discharge path, fluid contained in reservoir 12 is forced or pushed out of the reservoir 12 through filter 36 and into discharge tube 34. The fluid travels through fitting 38, spray tube 60 and out pressure valve 62.

Whether during storage of sprayer assembly 10 or during use thereof, the particulate matter suspended in the fluid held by reservoir 12 will tend to settle toward bottom 20. As described above, particulate and foreign matter will accumulate on and around filter 36. The settled and foreign accumulated particulate matter displaces fluid from the region surrounding filter 36 and, therefore, reduces the volume of fluid being discharged from, or completely clog, sprayer assembly 10. Increasing the pressure upon the fluid may only exacerbate the clog. The user of sprayer assembly 10, noticing reduced volume of fluid flow or a complete clog, simply rotates spray assembly 10 around its vertical axis in any direction. This rotation causes the fluid within reservoir 12 to rotate. When the rotating fluid encounters agitator 64, turbulence in the fluid is created in the region of the agitator. The turbulence maintains unsettled particulate matter in suspension within the fluid and returns settled particulate matter into suspension. Settling of the particulate matter and clogging of the sprayer can be prevented through preemptive rotation of sprayer assembly 10 around its vertical axis in any direction.

Due to the proximity of agitator 64 and filter 36, the region of turbulence created by agitator 64 encompasses the filter 36. The turbulence dislodges and returns to suspension the settled particulate matter surrounding filter 36. The user may alternately rotate the reservoir clockwise and then counterclockwise to increase turbulence. The portion of filter 36 which extends below agitator end 70 is subjected to both the fluid flowing around agitator 64 and the fluid flowing turbulently under agitator end 70, and is therefore subjected to increased turbulence which acts to further dislodge any settled particulate matter from the region surrounding the filter and any particulate matter lodged or settled against the filter itself. Thus, following a minimal number of rotations of sprayer 10 around its vertical axis in any direction the settled particulate matter is dispersed, and a full volume of fluid for the given pressure is once again being discharged from sprayer 10.

In the embodiment shown, reservoir 12 is shown and described as being substantially cylindrical in shape. However, it is to be understood that reservoir 12 can take other shapes, such as, for example, cubic or oval, and effectively perform its intended function.

Pump assembly 14 includes, in the embodiment shown, a handle 30 interconnected with pump mechanism 32 by shaft 33. It is to be understood that pump mechanism 14 can be alternatively configured to include, for example, a trigger interconnected with and activating the pump mechanism. Further, pump assembly 14 can be alternatively configured as an electronically controlled pump using buttons or switches to activate and deactivate the pump mechanism.

In the embodiment shown, filter 36 is shown as having a substantially cylindrical body 41 and a semispherical portion 44. However, it is to be understood that filter 36 can be alternatively configured and effectively perform its intended function. Filter 36 can be alternatively configured as, for example, a square cage filter. Furthermore, filter 36 is, in the embodiment shown, a separate component of sprayer assembly 10. However, it is to be understood that filter 36 and discharge tube 34 can be combined into one integral unit. Moreover, in the embodiment shown, filter 36 is attached to discharge tube 34 with an adhesive. However, it is to be understood that filter 36 can be alternatively configured to include a compressible gasket which enables the insertion of discharge tube 34 into filter 36 and which also prevents fluid and particulate matter from entering between the opening 42 of filter 36 and discharge tube 34.

Fitting 38 is, in the embodiment shown, a separate component of sprayer assembly 10 and includes threaded at outlet end 58 to receive sprayer tube 60. However, it is to be understood that outlet end 58 and sprayer tube 60 may be attached by other means, such as, for example, by use of adhesive or clamping. Reservoir 12 can be alternatively configured such that fitting 38 is integral therewith. Furthermore, fitting 38 can also be integrally formed with discharge tube 34, such as, for example, through injection molding. Moreover, the entire discharge path of sprayer assembly 10, i.e. filter 36, discharge tube 34, fitting 38, spray tube 60 and pressure valve 62 can be alternatively configured as one integral unit.

In the embodiment shown, agitator 70 is an elongate planar member. However, it is to be understood that agitator 70 can be alternatively configured to take a number of various shapes and sizes.

While this invention has been described as having a preferred design, the present invention can be further modified within the spirit and scope of this disclosure. This application is therefore intended to cover any variations, uses, or adaptations of the present invention using the general principles disclosed herein. Further, this application is intended to cover such departures from the present disclosure as come within the known or customary practice in the art to which this invention pertains and which fall within the limits of the appended claims.

What is claimed:

1. A sprayer assembly for dispensing a fluid having suspended therein particulate matter of a particulate size, said sprayer assembly comprising:

a reservoir having an interior including at least one side wall defining said interior, a bottom side and an exterior, said reservoir configured for containing the fluid in said interior, said reservoir defining a first opening for receiving the fluid and a second opening for dispensing the fluid;

a pump sealingly and removably received in said first opening, said pump including a pump handle disposed on said exterior and a pump mechanism disposed in said interior, said pump handle being connected to said pump mechanism, said pump being operable to increase a pressure in said interior;

a discharge tube defining a fluid passage, said discharge tube having a first end fluidly connected to said second opening and a second end disposed in said interior;

a filter having a plurality of filter passages of a predetermined size, said filter being disposed within said interior and being associated with said second end of said discharge tube, said predetermined size being selected such that said filter is configured for preventing particles larger than said particulate size from passing into said discharge tube; and at least one agitator disposed in said interior and attached to said at least one side wall and being configured for creating a fluid turbulence in a region of said interior surrounding said filter to thereby dislodge accumulated particles from said filter and from said region, said agitator comprising an agitator end disposed at a predetermined distance from the bottom of said reservoir and proximate said filter wherein at least a portion of said filter being disposed closer to s aid bottom side than said agitator end.

2. The sprayer assembly of claim 1, wherein said at least one agitator further comprises an elongate planar member having a first elongate edge and a second elongate edge, said first elongate edge being attached to said side wall, said elongate planer member extending a predetermined distance in to said interior.

3. The sprayer assembly of claim 1, wherein said filter is attached to said second end of said discharge tube.

4. The sprayer assembly of claim 1, wherein said filter includes a body having a filter end integral therewith, said body defining an opening in an end opposite said filter end, said second end of said discharge tube extending through said opening into said body towards said filter end such that said second end of said discharge tube is surrounded by said filter, said filter end and said second end of said discharge tube defining a gap therebetween.

5. The sprayer assembly of claim 4, wherein said gap is approximately one-quarter of an inch.

6. The sprayer assembly of claim 4, wherein said body is of a substantially cylindrical shape and said filter end is of a substantially semispherical shape.

7. The sprayer assembly of claim 1, further comprising a fitting sealingly received within said second opening of said reservoir, said fitting having an inlet side interconnected with an outlet side, said inlet side being disposed in said interior and said outlet side being disposed on said exterior, said fitting defining a fluid passage from said interior to said exterior, said first end of said discharge tube being attached to said inlet.

8. The sprayer assembly of claim 7, wherein said fitting is at least one of integral with and monolithic with said reservoir.

9. The sprayer assembly of claim 7, wherein said fitting is at least one of integral with and monolithic with said discharge tube.

10. A sprayer assembly for dispensing a fluid having suspended therein particulate matter of a particulate size, said sprayer assembly comprising:

a reservoir having an interior including at least one side wall defining said interior, a bottom side and an exterior, said reservoir configured for containing the fluid in said interior, said reservoir defining a first opening for receiving the fluid and a second opening for dispensing the fluid;

a pump sealingly and removably received in said first opening, said pump including a pump handle disposed on said exterior and a pump mechanism disposed in said interior, said pump handle being connected to said pump mechanism, said pump being operable to increase a pressure in said interior;

a discharge tube defining a fluid passage, said discharge tube having a first end fluidly connected to said second opening and a second end disposed in said interior;

a filter having a plurality of filter passages of a predetermined size, said filter being disposed within said interior and being associated with said second end of said discharge tube, said predetermined size being selected such that said filter is configured for preventing particles larger than said particulate size from passing into said discharge tube;

at least one agitator disposed in said interior and attached to said at least one side wall and being configured for creating a fluid turbulence in a region of said interior surrounding said filter to thereby dislodge accumulated particles from said filter and from said region, said agitator comprising an agitator end disposed at a predetermined distance from the bottom of said reservoir and proximate said filter wherein at least a portion of said filter being disposed closer to said bottom side than said agitator end;

a fitting sealingly received within said second opening of said reservoir, said fitting having an inlet side interconnected with an outlet side, said inlet side being disposed in said interior and said outlet side being disposed on said exterior, said fitting defining a fluid passage from said interior to said exterior, said first end of said discharge tube attached to said inlet; and a spray tube having a first end connected to said outlet side of said fitting and a second end terminated by a pressure valve, said pressure valve being operable to control the discharge of fluid from said interior.

11. An outlet assembly for a sprayer, the sprayer having an interior, an exterior, a first opening for receiving fluid, the fluid having particulate matter of a particulate size suspended therein, and a second opening for dispensing the fluid, said outlet assembly comprising:

a discharge tube defining a fluid passage, said discharge tube having a first end fluidly connected to the second opening of the sprayer and a second end disposed in the interior of the sprayer; and a filter having a plurality of filter passages of a predetermined size, said filter being disposed within said interior and being attached to said second end of said discharge tube, said predetermined size being selected such that said filter is configured for preventing particles larger than said particulate size from passing into said discharge tube;

wherein said outlet assembly includes a fitting sealingly received in the second opening of the sprayer, said fitting is at least one of integral with and monolithic with said discharge tube, said fitting having an inlet side interconnected with an outlet side, said inlet side being disposed in said interior and said outlet side being disposed on said exterior, said fitting defining a fluid passage from said interior to said exterior, said first end of said discharge tube being attached to said inlet side; and a spray tube having a first end connected to the second opening of the sprayer and a second end terminated by a pressure valve, said pressure valve being operable to control the discharge of fluid from the interior of the sprayer.

12. The outlet assembly of claim 11, wherein said filter includes a body having a filter end integral therewith, said body defining an opening in an end opposite said filter end, said second end of said discharge tube extending through said opening into said body towards said filter end such that said second end of said discharge tube is surrounded by said filter, said filter end and said second end of said discharge tube defining a gap therebetween.

13. The sprayer assembly of claim 12, wherein said gap is approximately one-quarter of an inch.

14. The outlet assembly of claim 12, wherein said body is of a substantially cylindrical shape and said filter end is of a substantially semispherical shape.

15. The outlet assembly of claim 11, wherein said first end of said spray tube is connected to said outlet side of said fitting.

16. The outlet assembly of claim 11, further comprising a spray tube having a first end connected to the second opening of the sprayer and a second end terminated by a pressure valve, said pressure valve being operable to control the discharge of fluid from the interior of the sprayer.

17. A method of dispensing a fluid having suspended therein particulate matter, said method comprising the steps of:

attaching an agitator to a sidewall defining an interior of a reservoir having a bottom wall, wherein said agitator being configured for creating a fluid turbulence in a region of said interior surrounding a filter to thereby dislodge accumulated particles from said filter and from said region, said agitator comprising an agitator end disposed at a predetermined distance from the bottom wall of said reservoir and proximate said filter wherein at least a portion of said filter being disposed closer to said bottom side than said agitator end;

filling an interior of a reservoir with the fluid;

providing a fluid discharge passage having a control valve, an intake end disposed within said interior, and an outlet end disposed externally of said interior;

sealing said reservoir;

increasing a pressure in said interior to thereby force the fluid into said discharge passage;

operating said control valve to selectively open and close said discharge passage;

filtering with a filter the fluid entering said intake end of said fluid discharge passage, said filter having a body and an integral filter end, said body defining an opening opposite said filter end, said intake end of said discharge passage extending through said opening into said body towards said filter end, said intake end being surrounded by said filter;

forming a gap between said filter end and said intake end; and agitating said fluid in a region surrounding said filter to dislodge particulate matter accumulated thereon and to return to suspension particulate matter that has settled out of suspension with the fluid, wherein said agitating step comprises rotating said reservoir about a vertical axis thereof.

18. The method of sprayingly dispensing a fluid having suspended therein particulate matter of a particulate size of claim 17, wherein said forming step comprises forming a gap between said filter end and said intake end of approximately one-quarter inch.

19. The method of sprayingly dispensing a fluid having suspended therein particulate matter of a particulate size of claim 17, wherein said agitating step comprises rotating said reservoir approximately four times about a vertical axis thereof.

* * * * *